(12) United States Patent
Halliyal et al.

(10) Patent No.: US 7,079,975 B1
(45) Date of Patent: Jul. 18, 2006

(54) SCATTEROMETRY AND ACOUSTIC BASED ACTIVE CONTROL OF THIN FILM DEPOSITION PROCESS

(75) Inventors: Arvind Halliyal, Sunnyvale, CA (US); Bhanwar Singh, Morgan Hill, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 235 days.

(21) Appl. No.: 09/845,231

(22) Filed: Apr. 30, 2001

(51) Int. Cl.
*G01B 11/02* (2006.01)
*G01B 15/02* (2006.01)

(52) U.S. Cl. .................... 702/172; 702/40; 438/16

(58) Field of Classification Search ............ 702/121, 702/40, 81–84, 170–172, 183, 188; 438/16–17, 438/29–32; 250/559.16–559.2; 356/337–343, 356/508–509, 237.2–237.6, 300–303, 326, 356/388, 394, 398
See application file for complete search history.

(56) References Cited

U.S. PATENT DOCUMENTS

| | | | | |
|---|---|---|---|---|
| 4,211,488 A | * | 7/1980 | Kleinknecht | 356/369 |
| 4,352,016 A | * | 9/1982 | Duffy et al. | 250/358.1 |
| 4,575,922 A | * | 3/1986 | Nemiroff | 438/7 |
| 4,652,757 A | * | 3/1987 | Carver | 250/360.1 |
| 5,042,952 A | * | 8/1991 | Opsal et al. | 356/432 |
| 5,089,774 A | * | 2/1992 | Nakano | 324/751 |
| 5,270,222 A | * | 12/1993 | Moslehi | 438/7 |
| 5,943,548 A | * | 8/1999 | Kim | 438/7 |
| 5,993,544 A | * | 11/1999 | Knauss et al. | 117/94 |
| 6,017,779 A | | 1/2000 | Miyasaka | 438/149 |
| 6,025,206 A | * | 2/2000 | Chen et al. | 438/16 |
| 6,038,525 A | * | 3/2000 | Maguire et al. | 702/172 |
| 6,094,275 A | * | 7/2000 | Lin | 356/445 |
| 6,096,135 A | | 8/2000 | Guo et al. | 118/729 |
| 6,136,165 A | | 10/2000 | Moslehi | 204/298.06 |
| 6,162,488 A | * | 12/2000 | Gevelber et al. | 427/8 |
| 6,285,971 B1 | * | 9/2001 | Shah et al. | 703/2 |
| 6,304,326 B1 | * | 10/2001 | Aspnes et al. | 356/369 |
| 6,452,678 B1 | * | 9/2002 | Thakur et al. | 356/394 |
| 6,453,264 B1 | * | 9/2002 | Maguire et al. | 702/172 |
| 6,513,151 B1 | * | 1/2003 | Erhardt et al. | 716/21 |
| 6,541,783 B1 | * | 4/2003 | Robinson et al. | 250/492.23 |

* cited by examiner

*Primary Examiner*—Marc S. Hoff
*Assistant Examiner*—Mary Catherine Baran
(74) *Attorney, Agent, or Firm*—Amin & Turocy, LLP

(57) ABSTRACT

A system for monitoring and controlling the deposition of thin films employed in semiconductor fabrication is provided. The system includes one or more acoustic and/or ultrasonic wave sources, each source directing waves onto one or more thin films deposited on a wafer. Waves reflected from the thin film is collected by a monitoring system, which processes the collected waves. Waves passing through the thin film may similarly be collected by the monitoring system, which processes the collected waves. The collected waves are indicative of the presence of impurities and/or defects in the deposited thin film. The monitoring system analyzes and provides the collected wave data to a processor, which determines whether adjustments to thin film deposition parameters are needed. The system also includes a plurality of thin film deposition devices associated with depositing thin films on the wafer. The processor selectively controls thin film deposition parameters and devices to facilitate regulating deposition.

10 Claims, 16 Drawing Sheets

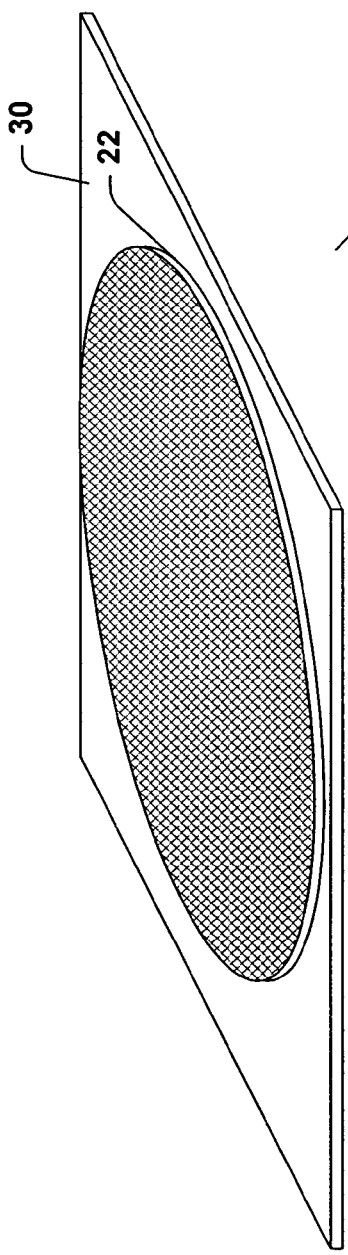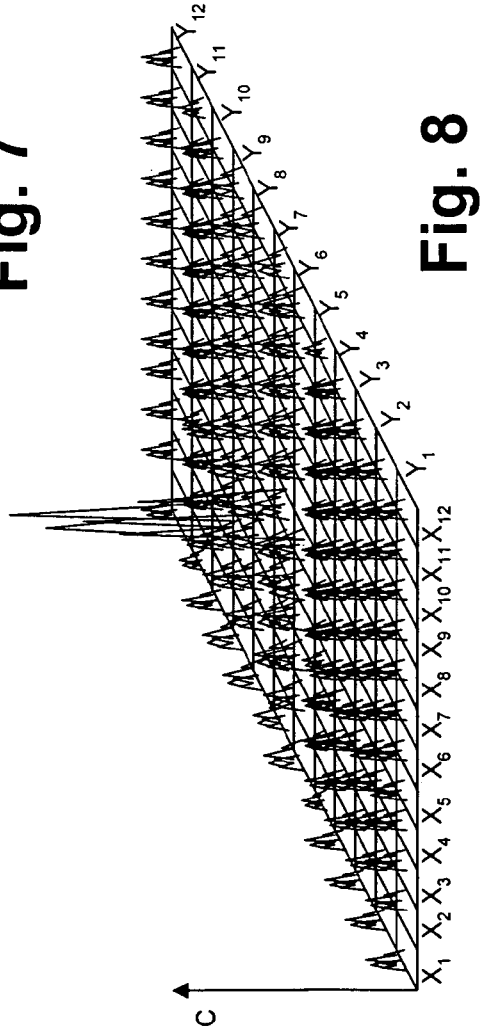
Fig. 7
Fig. 8
Fig. 9

SURFACE NORMAL    SPECULARLY REFLECTED BEAM

SCATTEROMETRY AND ACOUSTIC BASED ACTIVE CONTROL OF THIN FILM DEPOSITION PROCESS

TECHNICAL FIELD

The present invention generally relates to semiconductor processing, and in particular to a system for monitoring and controlling thin film deposition.

BACKGROUND

In the semiconductor industry, there is a continuing trend toward higher device densities. To achieve these high densities there have been, and continue to be, efforts toward scaling down device dimensions (e.g., at sub-micron levels) on semiconductor wafers. In order to accomplish such high device packing densities, smaller feature sizes and more precise feature shapes are required. This may include the width, thickness and spacing of interconnecting lines, spacing and diameter of contact holes, and the surface geometry, such as corners and edges, of various features.

The requirement of small features with close spacing between adjacent features requires sophisticated manufacturing techniques to ensure that quality and operability of the features are not compromised for the purpose of reducing feature size. Among the many aspects related to improving semiconductor fabrication processing to achieve higher density devices, the ability to deposit continuous, amorphous or crystalline thin films, which are substantially free from impurities and defects, remains critical to the structural integrity of smaller features as well as to the performance of the device with respect to increasing the speed of the device. Even minor impurities or defects present on the thin film layer tend to result in poor device characteristics, thereby reducing the effectiveness of the semiconductor device.

Several techniques for depositing thin films are known in the art. One exemplary technique for depositing a thin film is via chemical vapor deposition (CVD), wherein a wafer is introduced into a process chamber, heated to a desired temperature and gases are flown to initiate the deposition process. As in many conventional thin film deposition techniques, this CVD process inevitably permits the introduction of impurities into the deposited thin film layer. In CVD, a combination of inert carrier gasses and reactant gasses are introduced into the chamber wherein the elevated wafer temperature causes the reactive gasses to break down on the wafer surface thereby depositing the desired thin film on the wafer surface. To maintain the desired chemical reaction, the desired temperature in the chamber and at the wafer surface must be maintained. Accordingly, the wafer may be in continuous and direct contact with a means for heating the wafer. The means for heating the wafer (e.g. ceramic, quartz or metal susceptor) may release impurities into the deposition chamber, which may be deposited in the thin film layer. Conductive impurities can negatively impact the manufactured chip by, for example, producing electrical shorts, while non-conducting impurities can negatively impact the manufactured chip by, for example, increasing the resistance of conductive layers.

Another method for depositing thin films is via plasma enhanced chemical vapor deposition (PECVD). When PECVD is used to produce thin films, vapors including elements such as fluorine and carbon may be employed in cleaning the deposition chamber wherein the PECVD occurs. Remnants of the fluorine and carbon may remain in the deposition chamber after cleaning and thus may be incorporated into a thin film layer in subsequent deposition processes. Such impurities can negatively impact the quality of the manufactured chip by altering the desired electrical properties of and interactions between components on the manufactured chip. Novel deposition techniques are used for new materials employed in the semiconductor industry. For example, in deposition techniques such as MOCVD (Metal Organic Chemical Vapor Deposition), PLD (Pulsed Laser Deposition), ALCVD (Atomic Layer Chemical Vapor Deposition) and LPCVD (Low Pressure Chemical Vapor Deposition), which use liquid or solid precursors, the remnants of carbon or other unreacted organic or metal particles can be incorporated in the films, leading to failure of the device.

Thus, an efficient system and/or method to control thin film deposition and monitor defects and impurities in thin films are desired to increase quality and reliability in IC manufacture.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description presented later.

The present invention provides a system that facilitates monitoring defects and impurities in thin films and thus facilitates controlling thin film deposition in semiconductor manufacturing. Controlling the thin film deposition process with runtime feedback provides superior chip fabrication as compared to conventional systems and also facilitates achieving smaller feature sizes with improved geometry. Further, selectively marking wafers for further processing and/or rejection when a thin film has an unacceptable level of impurities and/or defects can increase chip consistency, quality and yield.

An exemplary system for monitoring defects and/or impurities in a thin film may employ one or more light sources arranged to project light onto one or more thin films being deposited on a wafer and one or more light sensing devices (e.g. photo detector, photodiode) for detecting light reflected by the one or more thin films. The light reflected from the one or more thin films is indicative of at least one parameter of the thin film deposition process (e.g. depth of film, uniformity of surface, presence of impurities, presence of defects, voids, agglomerates, large grains, second phase compositional variations, etc.).

An alternative exemplary system for monitoring defects and/or impurities in a thin film may employ one or more sources of acoustic and/or ultrasonic waves arranged to project acoustic and/or ultrasonic waves onto one or more thin films being deposited on a wafer and one or more acoustic and/or ultrasonic wave sensing devices (e.g. microphone) for detecting waves reflected by, and/or allowed to pass through the one or more thin films. The waves reflected from, and/or passing through the one or more thin films is indicative of at least one parameter of the thin film deposition process (e.g. depth of film, uniformity of surface, presence of impurities, presence of defects, voids, agglomerates, large grains, second phase compositional variations, etc.).

Yet another alternative exemplary system may employ the photo, acoustic and/or ultrasonic generating and detecting systems described above in combination.

One or more deposition components may be employed in fabricating a particular chip. It is to be appreciated by one skilled in the art that any suitable deposition components may be employed with the present invention. For example, deposition components including, but not limited to various types of chemical vapor deposition (CVD) components (e.g., LPCVD, MOCVD, ALCVD, etc.) and/or plasma enhanced chemical vapor deposition (PECVD) components may be employed in accordance with the present invention. The deposition components are selectively driven by the system to deposit a thin film to a desired thickness and/or uniformity within an acceptable level of defects and/or impurities. It is important to deposit enough thin film on a wafer to achieve the desired properties, therefore the thickness or amount of thin film deposited must be considered. As the non-uniformity of the thin film layer increases, performance and speed of the device decreases. Thus, controlling the deposition components such as thickness, uniformity, and acceptable levels of defects and/or impurities facilitates achieving faster and higher density devices.

The present invention operates by comparing signatures generated by light reflected by the thin film to desired signatures. By comparing desired signatures to measured signatures, runtime feedback may be employed to more precisely control the thin film deposition, and to identify and reject wafers upon which a thin film has been deposited with unacceptable levels of defects and/or impurities. Alternatively, or in addition, acoustic techniques may also be used as described above. As a result, higher quality monitoring and controlling of thin film deposition is achieved, which in turn increases performance and yield of the chip.

In accordance with one aspect of the present invention, a system for controlling a thin film deposition process is provided, the system comprising: one or more thin film deposition components operative to deposit a thin film on one or more portions of a wafer; a thin film deposition component driving system for driving the one or more deposition components; a system for directing light on to the wafer; a monitoring system adapted to detect structural irregularities associated with the deposited thin film by comparing reflected light data with a database comprising known thin film reflected light signatures; and a processor operatively coupled to the monitoring system and the thin film deposition component driving system, wherein the processor receives data from the monitoring system and communicates deposition parameter adjustments to the one or more deposition components according to the received data, thereby facilitating regulating thin film deposition.

In accordance with another aspect of the present invention, a system for controlling a thin film deposition process is provided. The system includes thin film deposition components operative to deposit a thin film on one or more portions of a wafer; a thin film deposition component driving system for driving the one or more deposition components; a system for directing acoustic and/or ultrasonic waves on to the wafer; a monitoring system adapted to detect structural irregularities associated with the deposited thin film by comparing reflected wave data with a database comprising known thin film reflected wave signatures; and a processor operatively coupled to the monitoring system and the thin film deposition component driving system, wherein the processor receives data from the monitoring system and communicates deposition parameter adjustments to the one or more deposition components according to the received data, thereby facilitating regulating thin film deposition.

Yet another aspect of the present invention provides a system for controlling a thin film deposition process. The system includes thin film deposition components operative to deposit a thin film on portions of a wafer; a thin film deposition component driving system for driving the one or more deposition components; a system for directing acoustic and/or ultrasonic waves on to the wafer; a monitoring system adapted to detect structural irregularities associated with the deposited thin film by comparing reflected wave data with a database comprising known thin film reflected wave data signatures; a system for directing light on to the wafer; a monitoring system adapted to detect structural irregularities associated with the deposited thin film by comparing reflected light data with a database comprising known thin film reflected light signatures; and a processor operatively coupled to the monitoring system and the thin film deposition component driving system, wherein the processor receives data from the monitoring system and communicates deposition parameter adjustments to the one or more deposition components according to the received data, thereby facilitating regulating thin film deposition.

Still yet another aspect of the present invention provides a method for monitoring and controlling the deposition of a thin film, comprising: depositing a thin film on a wafer; directing a light onto the thin film; collecting a light reflected from the thin film; employing scatterometry means to analyze the reflected light to determine one or more properties of the thin film; and controlling a deposition component to deposit thin film on the wafer.

Still another aspect of the present invention provides a method for monitoring and controlling the deposition of a thin film. The method includes depositing a thin film on a wafer; directing acoustic and/or ultrasonic waves onto the thin film; collecting waves reflected from the thin film; employing acoustic and/or ultrasonic techniques to analyze the reflected acoustic and/or ultrasonic waves to determine one or more properties of the thin film; and controlling a deposition component to deposit thin film on the wafer.

Yet another aspect of the present invention provides a method for regulating a process for depositing a thin film, comprising: using one or more deposition components to deposit a thin film; determining the acceptability of the thin film deposition; and using a processor to coordinate control of the one or more deposition components to deposit the thin film.

Another aspect of the present invention provides a system for regulating a process for depositing a thin film, comprising: means for using one or more deposition components to deposit a thin film; means for determining the acceptability of the thin film deposition; and means for using a processor to coordinate control of the one or more deposition components to deposit the thin film.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The present invention is illustrated by way of example in the accompanying figures in which:

FIG. 7 is a perspective illustration of a wafer that may be fabricated in accordance with an aspect of the present invention;

FIG. 8 is a representative three-dimensional grid map of a thin film illustrating signature measurements taken at grid blocks of the thin film in accordance with an aspect of the present invention;

FIG. 9 is a signature measurement table correlating the measurements of FIG. 8 with desired values for the measurements in accordance with the present invention;

DETAILED DESCRIPTION

Figure 1:
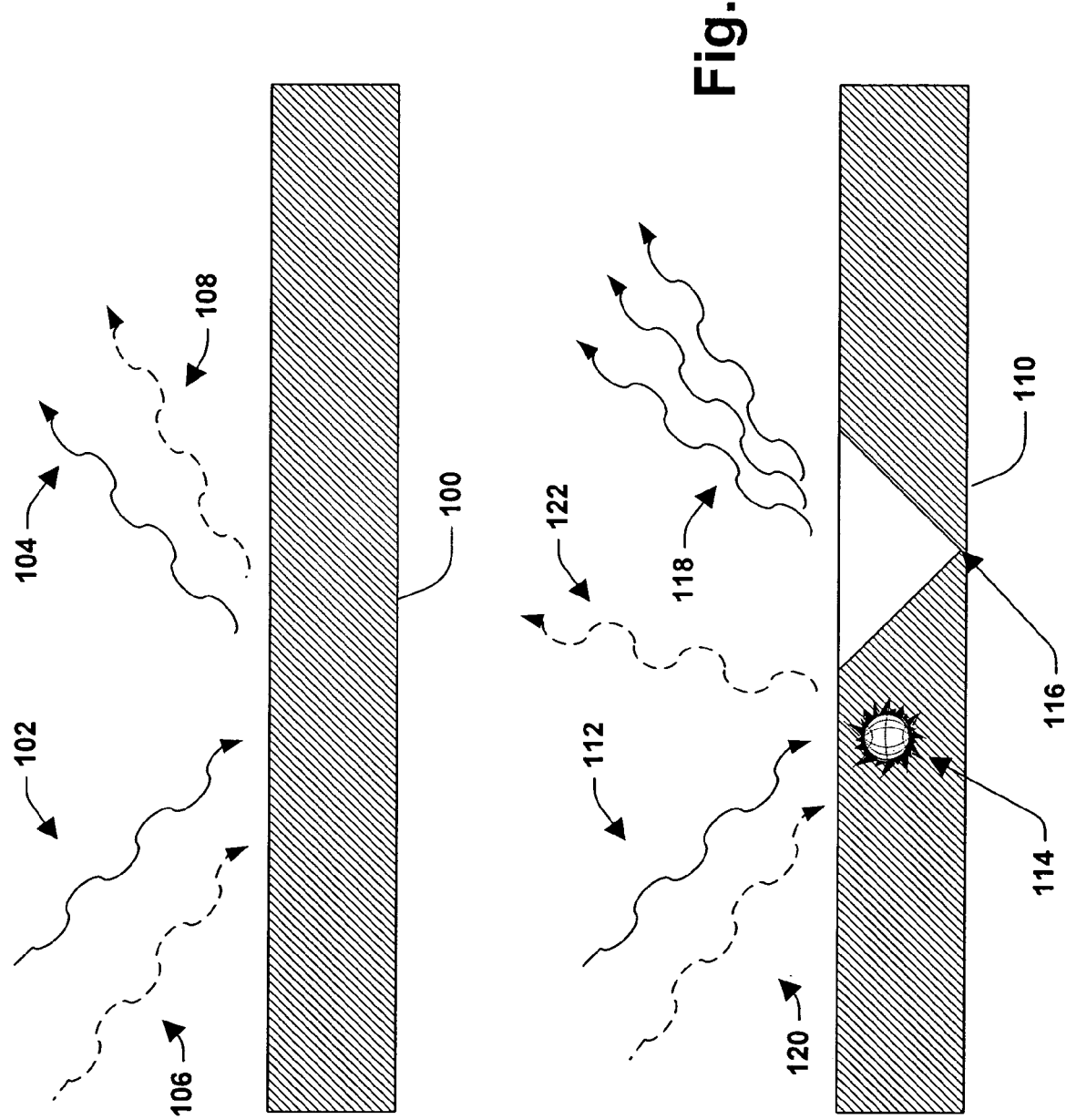
FIG. 1 is a simplified schematic diagram of light and/or acoustic waves reflecting from a wafer.

The present invention will now be described with reference to the drawings, wherein like reference numerals are used to refer to like elements throughout. The following detailed description is of the best modes presently contemplated by the inventors for practicing the invention. It should be understood that the description of these aspects are merely illustrative and that they should not be taken in a limiting sense.

Referring initially to FIG. 1, two types of exemplary deposited thin films are shown. FIG. 1 shows a thin film 100, having substantially no imperfections, being subjected to a scatterometry based monitoring system. The monitoring system will be described in greater detail later. One or more beams of light 102 are directed at the thin film 100 and are reflected off the thin film as reflected light 104. Relationships including, but not limited to, an angle of incidence of the light 102 with the thin film 100, an angle of reflection of the reflected waves 104 and the thin film 100, an intensity of the directed light 102, an intensity of the reflected light 104, and diffraction patterns produced by the reflected light 104 may be employed to generate signatures related to uniformity, thickness, presence and/or absence of impurities, defects and agglomerates, for example, in the thin film 100. Similarly, acoustic and/or ultrasonic waves 106 may be directed at the thin film 100 as shown in FIG. 1. The corresponding reflected waves 108 are also shown. Relationships including, but not limited to, angle of incidence of the acoustic and/or ultrasonic waves 106 and the thin film 100, angle of reflection of the reflected waves 108, and intensity of the waves 108 may similarly be employed to generate signatures related to the uniformity, thickness, and the presence or absence of impurities and defects in the thin film 100.

FIG. 1 also illustrates a thin film 110 having an impurity 114 and a defect 116. The impurity 114 may be, for example, fluorine, carbon, or other residual or metal particles deposited on or in the thin film during processing. The defect 116 may be an area where thin film was not deposited amorphously and/or uniformly. Such defects include any structural irregularity resulting from deposition such as a pinhole, an air bubble, a depression, an agglomerate and the like. The defect 116 may also be an area where thin film was deposited unevenly or not at all. One or more beams of light 112 are directed at the thin film 110 and are reflected and/or diffracted from the thin film 110 as reflected light 117. The reflection and/or diffraction of the light 112 may be affected by the presence of the impurity 114 and/or the defect 116. Similarly, acoustic and/or ultrasonic waves 118 are directed at the thin film 110 and are reflected and/or scattered by the thin film 110 as waves 119. The reflection and/or scattering of the acoustic and/or ultrasonic waves 118 may be affected by the presence of the impurity 114 and/or the defect 116.

Figure 2:
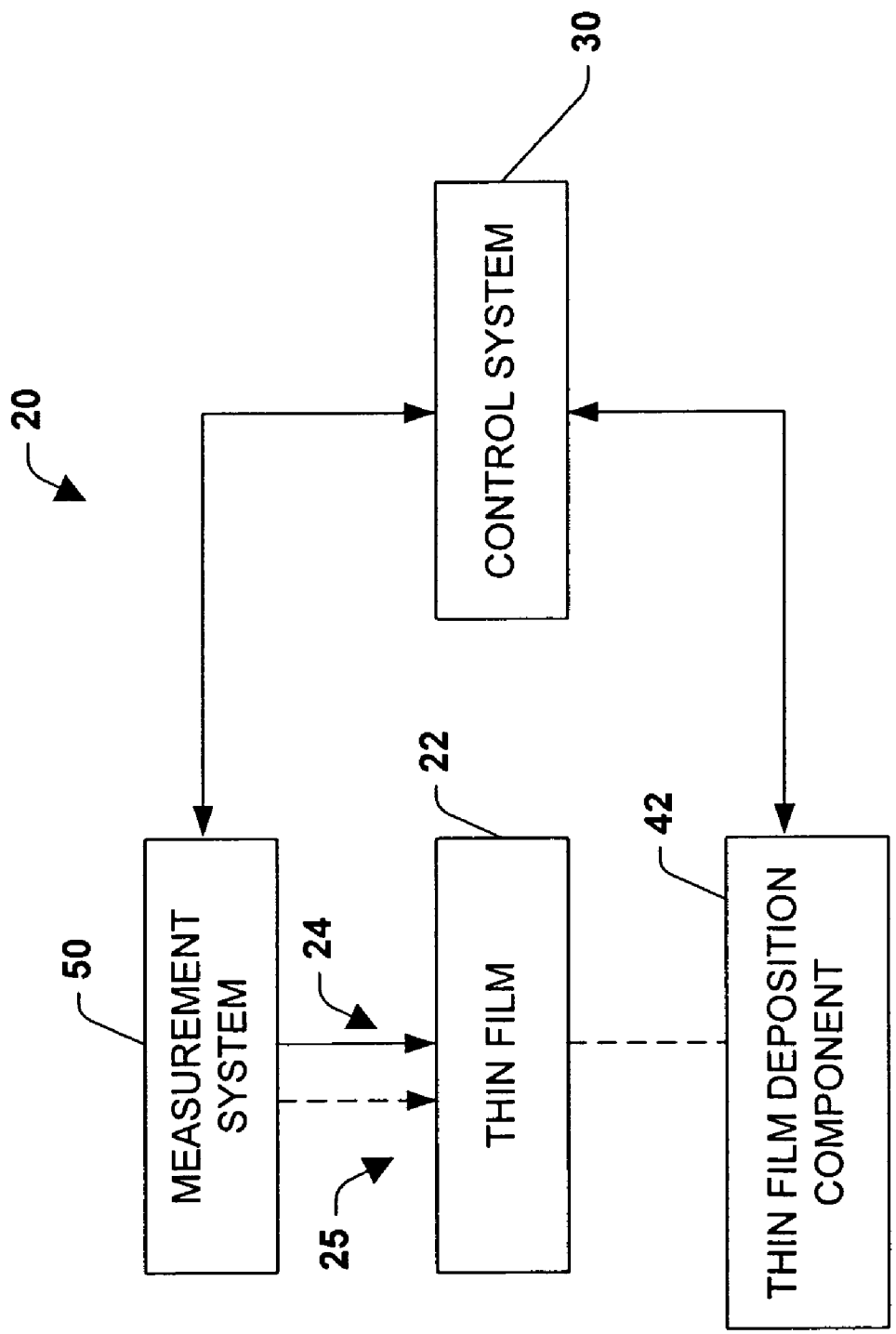
FIG. 2 is a simplified block diagram of a monitoring and controlling system in accordance with an aspect of the present invention.

In order to monitor and regulate thin film deposition to mitigate structural irregularities present in deposited thin film, a regulating system 20 may be employed. FIG. 2 shows a block diagram of an exemplary regulating system 20. The system 20 facilitates monitoring a thin film 22 for impurities and/or defects in accordance with one aspect of the present invention. The thin film 22 is operatively coupled to a thin film deposition component 42, which for example, is able to deposit a thin film via well-known techniques including, but not limited to, CVD, PECVD, MOCVD and ALCVD. The deposition component 42 is controlled by a thin film deposition driver system 80 (FIG. 3).

The system 20 also includes a monitoring system 50 operable to detect the presence or absence of impurities and/or defects in the thin film 22 in accordance with one aspect of the present invention. The monitoring system 50 includes, for example, a light source that emits a beam 24 incident to the surface of the thin film 22. The beam 24 interacts with the thin film 22 and is reflected and/or diffracted. The monitoring component 50 also includes a detection system for detecting the reflected and/or diffracted light (also indicated at 24 for purposes of brevity). Characteristics of the thin film 22 are determined based on the properties of the reflected and/or diffracted light 24. The monitoring system 50 may further include, for example, a source for generating acoustic and/or ultrasonic waves that emits a wave 25 incident to the surface of the thin film 22. The wave 25 interacts the thin film 22 and is reflected and/or scattered. The monitoring system 50 also includes a detection system for detecting the reflected and/or diffracted wave (also indicated at 25 for purposes of brevity). In addition, the monitoring system 50 is adapted to detect structural irregularities associated with the deposited thin film by comparing reflected light data associated with the deposited thin film with a database comprising known thin film reflected light signatures. Characteristics of the thin film 22 are determined based on the properties of the reflected and/or diffracted sound 25.

The system 20 also includes a control system 30 operatively coupled to the thin film deposition component 42 and the monitoring system 50. The control system 30 which includes a processor and a memory, is programmed and/or configured to control operation of the thin film deposition component 42 in accordance with an aspect of the present invention.

Figure 3:
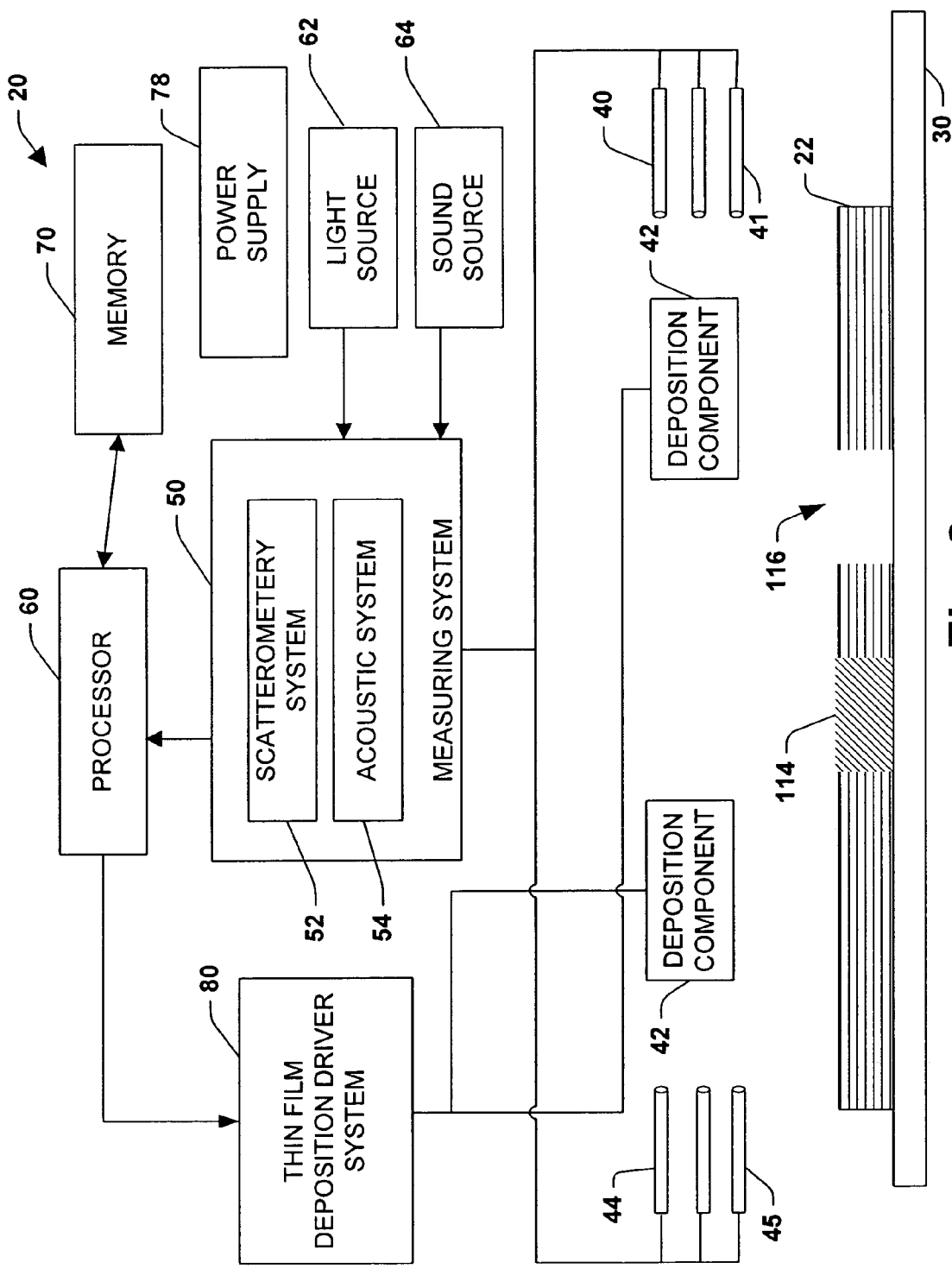
FIG. 3 is a schematic block diagram of a monitoring and controlling system in accordance with an aspect of the present invention.

Turning now to FIG. 3, the system 20 for monitoring and controlling thin film deposition is shown in greater detail. As discussed with respect to FIG. 2, one or more deposition components 42 deposit the thin film 22 using any suitable thin film deposition component in the present invention. One or more light sources 44 direct light onto on or more portions of the thin film 22. Light reflected from and/or passing through the thin film 22 is collected by one or more light detecting components 40, and processed by the monitoring system 50 to detect at least one parameter relating to the thin film deposition process (e.g. presence of impurities, presence of defects, thickness, uniformity). The reflected light is processed with respect to the incident light by the monitoring system 50. Variations in thickness and uniformity and presence of impurities and/or defects will cause the reflected light to be reflected and/or diffracted in different, quantifiable signatures. These collected signatures may then be used to allow feedback control of the deposition components 42 via the thin film deposition component driving system 80.

The monitoring system 50 also includes a scatterometry system 52. It is to be appreciated that any suitable scatterometry system may be employed to carry out the present invention and such systems are intended to fall within the scope of the claims appended hereto.

A light source 62 (e.g., a laser) provides light to the one or more light sources 44 via the monitoring system 50. One example of the light source 62 is a frequency-stabilized laser; however, it should be appreciated that any laser or other light source (e.g., laser diode or helium neon (HeNe) gas laser) suitable for carrying out the present invention may be employed. One or more light detecting components 40 (e.g., photo detector, photo diodes) collect light reflecting from the thin film 22.

Alternatively, or in addition, one or more acoustic and/or ultrasonic wave sources 45 may also project waves onto respective portions of the thin film 22. Waves reflected from and/or passing through the thin film 22 are collected by one or more wave detecting components 41, and processed by a monitoring system 50 to measure at least one parameter relating to the thin film deposition process (e.g. presence of impurities, presence of defects, thickness, uniformity). The reflected and/or passed through acoustic and/or ultrasonic waves are processed with respect to the incident waves in monitoring the various parameters. Thickness, uniformity and presence of impurities and/or defects will cause the reflected and/or passed through waves to be reflected and/or scattered in different, quantifiable manners. The reflected and/or passed through waves thus generate signatures, which can be used to facilitate feedback control of the deposition components 42 via a thin film deposition component driving system 80. The monitoring system 50 includes an acoustic/ultrasonic system 54. It is to be appreciated that any suitable acoustic/ultrasonic system may be employed to carry out the present invention and such systems are intended to fall within the scope of the claims appended hereto. Acoustic systems are well known in the art, and therefore further discussion related thereto is limited for the sake of brevity. It is to be appreciated that ultrasonic imaging techniques can also be used to produce an image of a defect.

A source of acoustic and/or ultrasonic waves 64 provides waves to the one or more acoustic and/or ultrasonic wave sources 45 via the monitoring system 50. One or more wave detecting components 41 (e.g., microphone) collect waves reflecting from and/or passing through the thin film 22.

Regardless of whether light, acoustic waves and/or ultrasonic waves are employed, the monitoring system 50 is adapted to detect structural irregularities associated with the deposited thin film by comparing the reflected data associated with the deposited thin film with a database (not shown) comprising known thin film reflected light, acoustic and/or ultrasonic wave signatures.

The processor 60 receives the data from the monitoring system 50 and determines which deposition components require adjustment according to the received data. To make this determination, the processor may employ a non-linear training system (not shown). The non-linear training system is operatively coupled to the processor 60. Once the processor 60 makes the determination, the processor 60 communicates deposition parameter adjustments to a deposition component driving system 80. The processor 60 is coupled to the thin film deposition component driving system 80 that drives the deposition components 42. The processor 60 controls the thin film deposition component driving system 80 to selectively regulate the deposition components 42. Furthermore, because the processor 60 is operatively coupled to the monitoring system 50, it may be programmed to control and operate the various components within the system 20 in order to carry out the various functions described herein.

The processor 60, (or central processing unit), may be any of a plurality of processors, such as the AMD K7 and/or other similar and compatible processors. The manner in which the processor 60 can be programmed to carry out the functions relating to the present invention will be readily apparent to those having ordinary skill in the art based on the description provided herein.

Still referring to FIG. 3, a memory 70, which is operatively coupled to the processor 60, is also included in the system 20 and serves to store program code executed by the processor 60 for carrying out operating functions of the system 20 as described herein. The memory 70 also serves as a storage medium for temporarily storing information such as thin film depth, thin film uniformity, presence of defects, presence of impurities, scatterometry information, wave information and other data that may be employed in carrying out the present invention. Furthermore, a power supply 78 provides operating power to the system 20. Any suitable power supply (e.g., battery, line power) may be employed to carry out the present invention.

Figure 4:
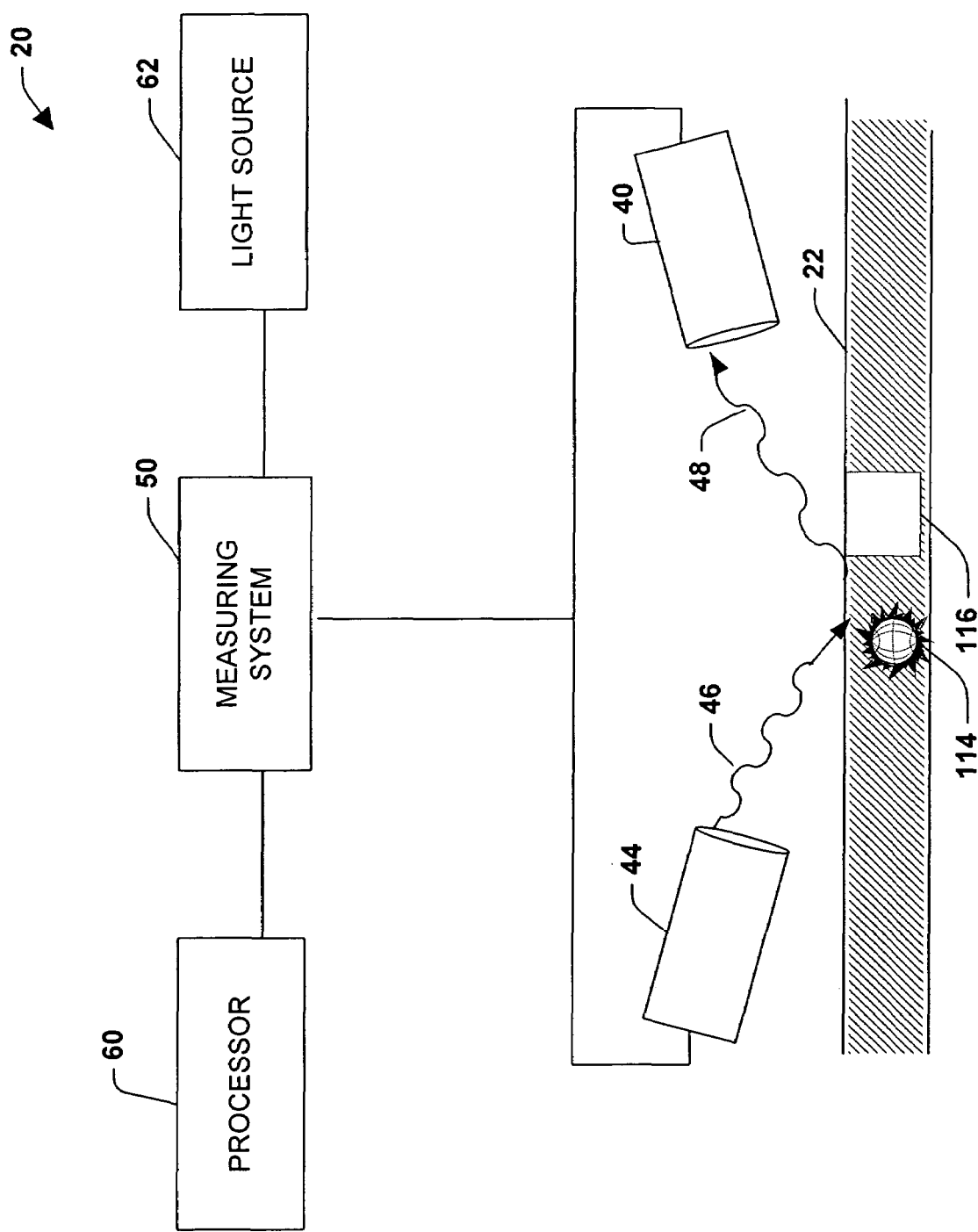
FIG. 4 is a partial schematic block diagram of the system of FIG. 3 illustrating one example system for monitoring thin film deposition in accordance with an aspect of present invention.

Turning now to FIG. 4, the system 20 is illustrated being employed to monitor and detect properties of the thin film 22 via light reflected from the thin film 22. The light source 44 directs a light 46 incident to the surface of the thin film 22. The angle of a light 48 reflected and/or diffracted from the surface of the thin film 22 will vary in accordance with the thickness, uniformity, and the presence of defects and/or impurities in the thin film 22. The one or more light detecting components 40 collect the reflected and/or diffracted light 48, pass the collected light, and/or data concerning the collected light, to the monitoring system 50, which processes the reflected light 48 and/or data concerning the reflected light 48 in accordance with scatterometry techniques to provide the processor 60 with data corresponding to the thickness, uniformity, and the presence of defects and/or impurities in the thin film 22. The reflected light 48 may generate a signature that can be compared to one or more signatures to determine whether the deposition process should continue.

Figure 5:
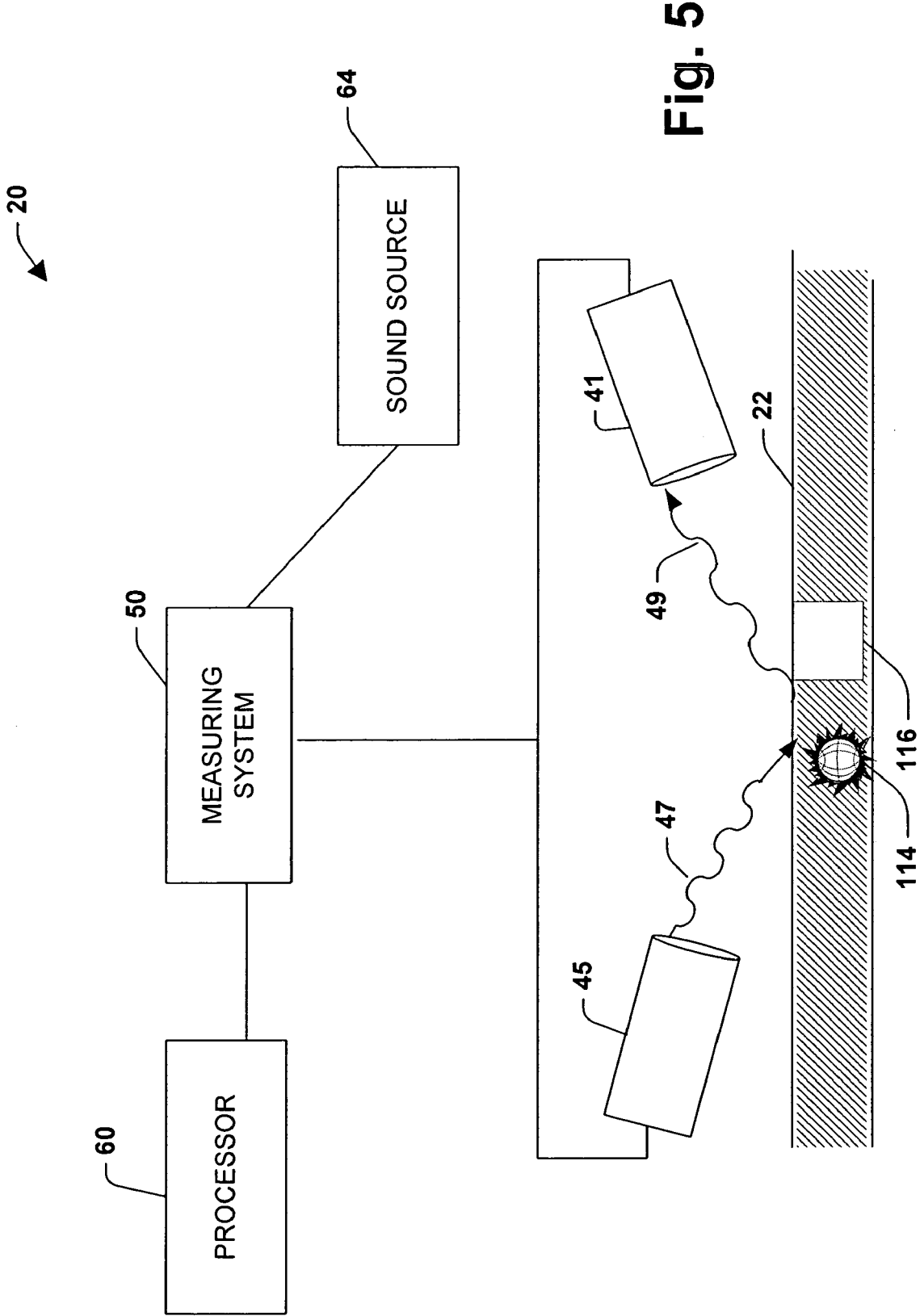
FIG. 5 is a partial schematic block diagram of the system of FIG. 3 illustrating another example system for monitoring thin film deposition in accordance with an aspect of present invention.

Turning now to FIG. 5, the system 20 is illustrated being employed to measure properties of the thin film 22 via waves reflected from the thin film 22. The acoustic and/or ultrasonic wave source 45 directs a wave 47 (acoustic and/or ultrasonic) incident to the surface of the thin film 22. The angle of a wave 49 reflected and/or scattered from the surface of the thin film 22 will vary in accordance with the thickness, uniformity, and the presence of defects and/or impurities in the thin film 22. The one or more wave detecting components 41 collect the reflected and/or scattered wave 49, pass the collected wave, and/or data concerning the collected wave, to the monitoring system 50, which processes the reflected wave 49 and/or data concerning the reflected wave 49 in accordance with acoustic and/or ultrasonic techniques to provide the processor 60 with data corresponding to the thickness, uniformity, and the presence of defects and/or impurities in the thin film 22. The reflected wave 49 may generate a signature that can be compared to one or more signatures to determine whether the deposition process should continue.

Figure 6:
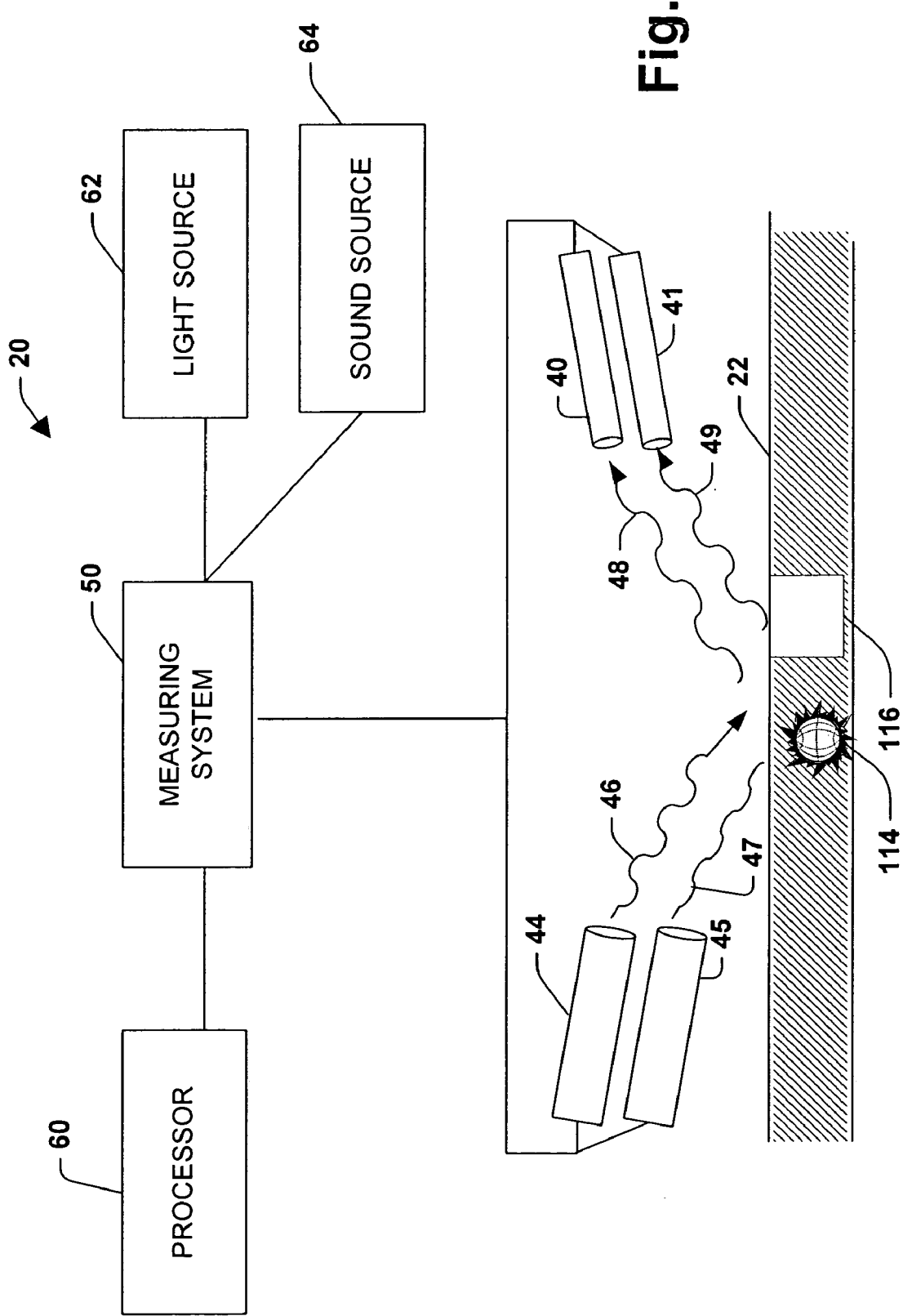
FIG. 6 is a partial schematic block diagram of the system of FIG. 3 illustrating another example system for monitoring thin film deposition in accordance with an aspect of present invention.

Turning now to FIG. 6, the system 20 is illustrated being employed to measure the properties of the thin film 22 via light, acoustic and/or ultrasonic waves as described above in connection with FIG. 4 and FIG. 5. In FIG. 6, the monitoring system 50 may employ light, acoustic waves and/or ultrasonic waves, and thus scatterometry, acoustic and/or ultrasonic techniques, to provide the processor 60 with data corresponding to the thickness, uniformity, and the presence of defects and/or impurities in the thin film 22. The reflected light 48 and/or the wave 49 may generate a signature that can be compared to one or more signatures to determine whether the deposition process should continue.

Referring now to FIGS. 7–9, another aspect of the present invention is shown. In addition to the methods described above, the thin film 22 may be partitioned into grid blocks to facilitate determining the position or location of defects, impurities, and variations in thickness and uniformity. Obtaining such positions or locations may facilitate the processor 60 in determining the deposition process parameter adjustments. In FIG. 7, a chuck 30 is shown in perspective supporting a thin film 22. The thin film 22 may be divided into a grid pattern as shown in FIG. 8. Each grid block (XY) of the grid pattern corresponds to a particular portion of the thin film 22. Each portion is individually monitored for thin film properties, (e.g. thickness, uniformity, presence of defects, presence of impurities).

In FIG. 8, thin film properties (e.g. thickness, uniformity, presence of defects, presence of impurities) associated with one or more portions of the thin film 22 ($X_1Y_1 \ldots X_{12}, Y_{12}$) are monitored by employing reflective light, acoustic and/or ultrasonic waves and the monitoring system 50. The signatures for the portions are shown in FIG. 8. Although FIG. 8 illustrates the thin film 22 being mapped (partitioned) into 144 grid block portions, the thin film 22 may be mapped with any number of portions suitable to carry out the present invention.

Given the set of signatures recorded in FIG. 8, the processor 60 may determine that an undesirable thin film thickness, uniformity, defect and/or impurity condition exists. Accordingly, the processor 60 may direct the deposition driver system to drive one or more thin film deposition components 42 to bring the thin film 22 to a desired thickness and/or uniformity and/or to correct one or more defects. It is to be appreciated that the deposition components 42 may be driven so as to increase or decrease the rate and/or temperature of deposition. When the processor 60 determines that the deposition process, as determined by analyzing the signatures, has reached a desired condition, the processor 60 may terminate deposition parameter adjustments. In addition, the processor 60 may direct the system 20 to reject a wafer having an unacceptable deposited thin film or the processor 60 may selectively mark such wafer for rejection. Such determinations made by the processor 160 may be made using a non-linear training system (not shown).

FIG. 9 illustrates an exemplary table of acceptable and unacceptable signatures. It can be seen that all the signatures are acceptable except a signature for grid $X_7Y_6$. The set of signatures depicted in FIG. 9 can be analyzed collectively as a master signature, can be analyzed in subsets to evaluate, for example, intermediate deposition and/or can be analyzed individually to determine whether an unacceptable or acceptable deposition condition exists. The analysis of the thin film signatures is used to control the thin film deposition component driving system 80.

Figure 10:
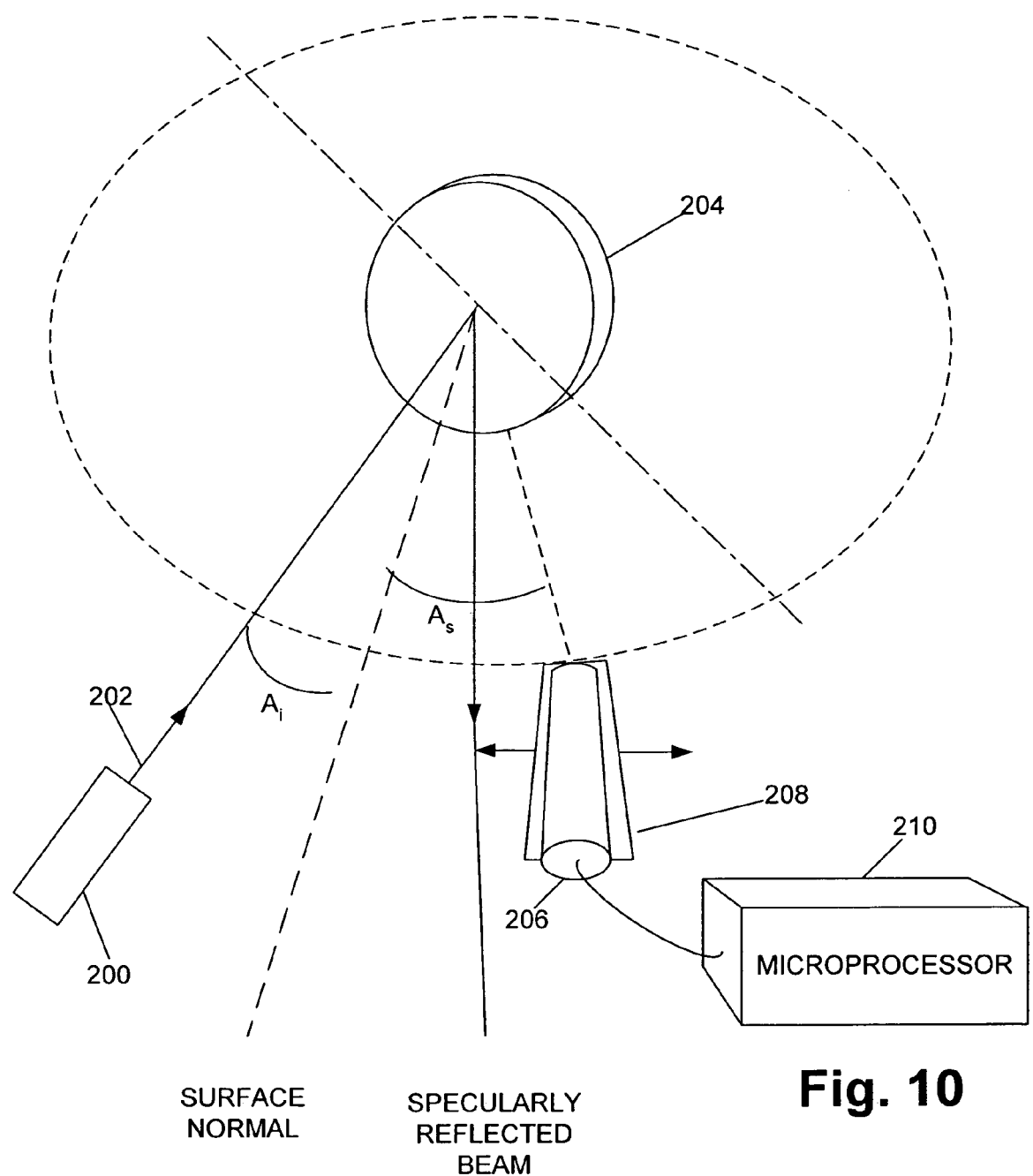
FIG. 10 illustrates an exemplary scatterometry system collecting reflected light in accordance with an aspect of the present invention.

FIG. 10 illustrates an exemplary scatterometry system collecting reflected light.

Light from a laser 200 is brought to focus in any suitable well-known manner to form a beam 202. A sample, such as a wafer 204 is placed in the path of the beam 202 and a photo detector or photo multiplier 206 of any suitable well-known construction. Different detector methods may be employed to determine the scattered power. To obtain a grating pitch, the photo detector or photo multiplier 206 may be mounted on a rotation stage 208 of any suitable well-known design. A microprocessor 210, of any suitable well-known design, may be used to process detector readouts, including, but not limited to, angular locations of different diffracted orders leading to diffraction grating pitches being calculated. Thus, light reflected from the sample 204 may be accurately measured.

Figure 11:
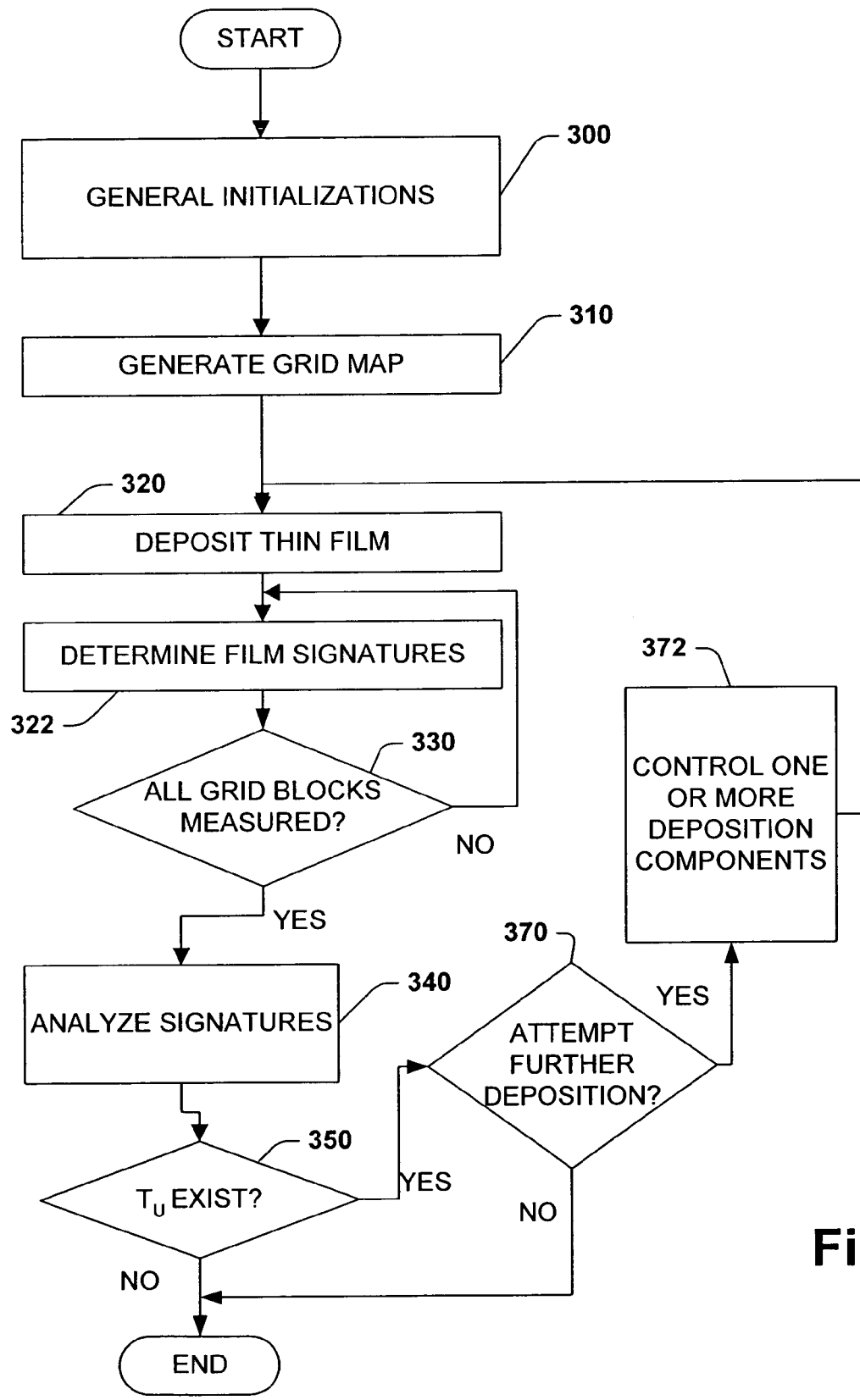
FIG. 11 is a flow diagram illustrating an example methodology for monitoring defects and/or impurities in a thin film and for controlling thin film deposition in accordance with an aspect of the present invention.
Figure 12:
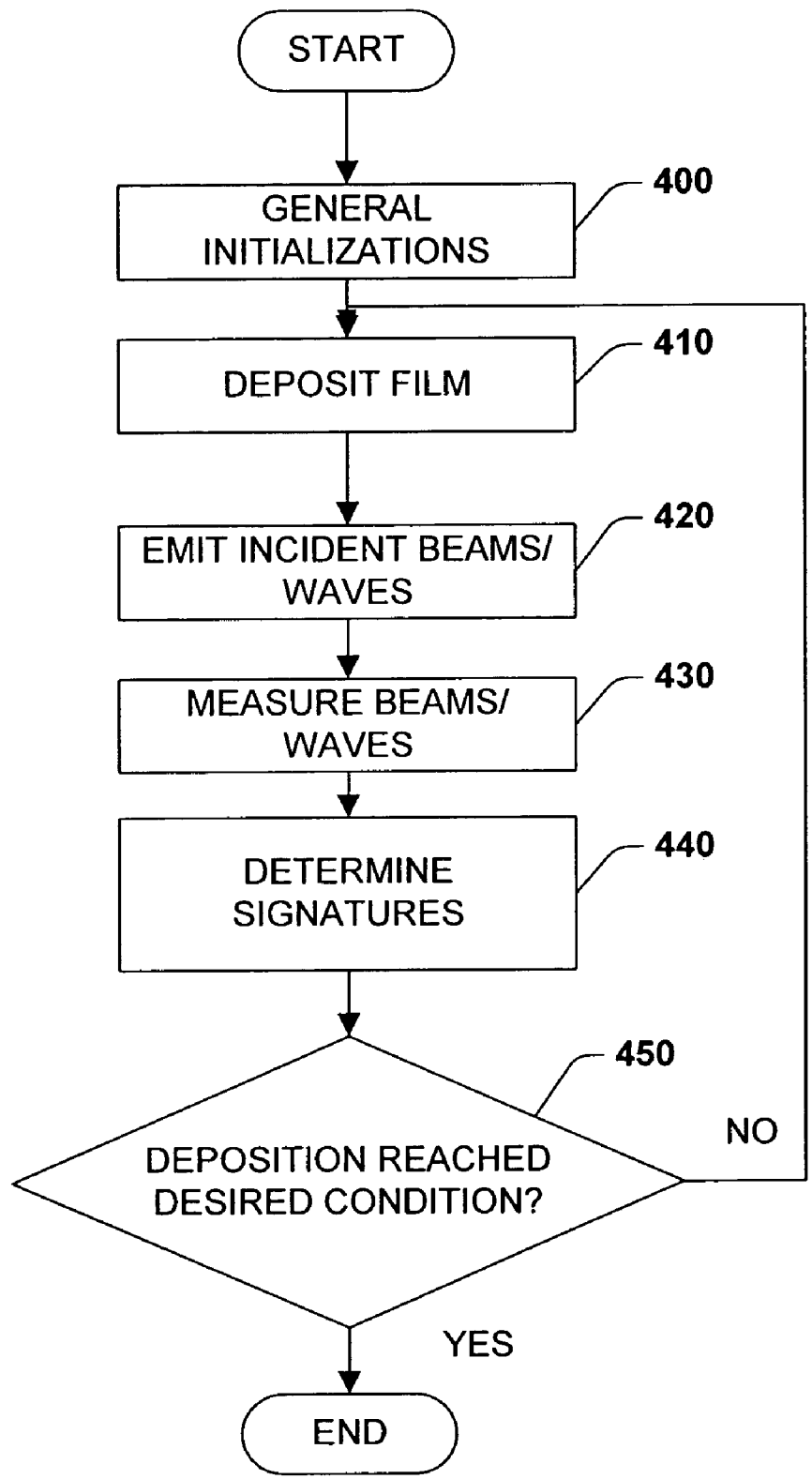
FIG. 12 is a flow diagram illustrating another example methodology for monitoring defects and/or impurities in a thin film and for controlling thin film deposition in accordance with an aspect of the present invention.

In view of the exemplary systems shown and described above, a methodology, which may be implemented in accordance with the present invention, will be better appreciated with reference to the flow diagrams of FIGS. 11 and 12. For purposes of simplicity of explanation, the methodologies of FIGS. 11 and 12 are shown and described as a series of blocks; however, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention.

FIG. 11 is a flow diagram illustrating one particular methodology for carrying out the present invention. At 300, a processor performs general initializations to a system for monitoring a thin film for defects and/or impurities. At 310, the processor maps at least a portion of a mask into a plurality of grid blocks "XY". At 320, the thin film deposition process is begun. At 322, signature determinations are made with respect to the various wafer portions mapped by the respective grid blocks XY. At 330, the processor determines if all grid block signatures have been taken. If no, the processor returns to step 322. If yes, then at 340 the processor analyzes the signature or signatures against a table of acceptable signatures. At 350, the processor determines if the signatures are acceptable. If the signatures are acceptable, the processor ends the iteration of the deposition process. If at 350 an unacceptable signature is found, the processor advances to 370 where a determination is made concerning whether further deposition attempts will be made. If no further attempts are to be made, then the wafer can be marked for further processing and/or rejection and alarms may be sent to subsequent methods and/or apparatus concerning the unacceptably deposited portion of the mask, after which the deposition process concludes. If the determination at 370 is YES, then at 372 the processor controls relevant deposition components to further deposit thin film. The present iteration is then ended and the process returns to 320 to perform another iteration.

FIG. 12 is a flow diagram illustrating another particular methodology for carrying out the present invention. At 400 general initializations and/or configurations are performed. At 410, the thin film deposition begins. At 420, incident light beams, acoustic waves and/or ultrasonic waves are emitted onto the thin film and at 430 the reflected and/or scattered beams and/or waves are measured. At 440, the signatures from the thin film upon which the incident beams and/or waves of 420 were directed are analyzed. At 450 a determination is made concerning whether the thin film deposition has produced a desired result. If the determination at 450 is YES, then the deposition terminates. If the determination at 450 is NO, then processing returns to 410. It is to be appreciated that while the blocks in FIG. 12 are shown in a linear order, emitting the incident beams and/or waves, collecting the reflected and/or diffracted beams and/or waves and determining whether the deposition process has produced a thin film with a desired thickness, uniformity and/or impurity levels may occur simultaneously, in situ.

Scatterometry is a technique for extracting information about a surface upon which an incident light has been directed. Information concerning properties including, but not limited to, dishing, erosion, profile, chemical composition, thickness of thin films and critical dimensions of features present on a surface such as a wafer can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 13:
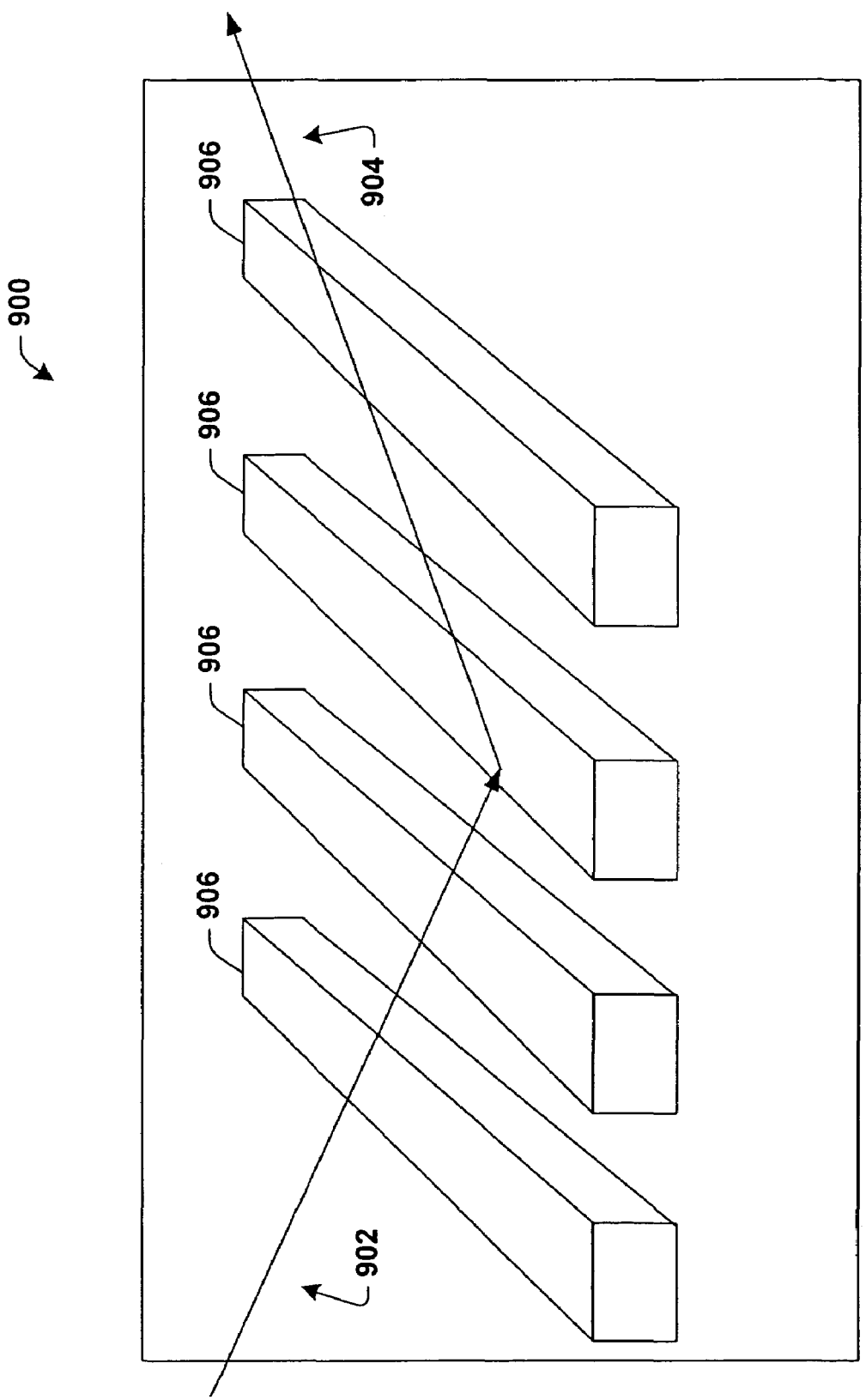
FIG. 13 is a simplified perspective view of an incident light reflecting off a surface, in accordance with an aspect of the present invention.
Figure 18:
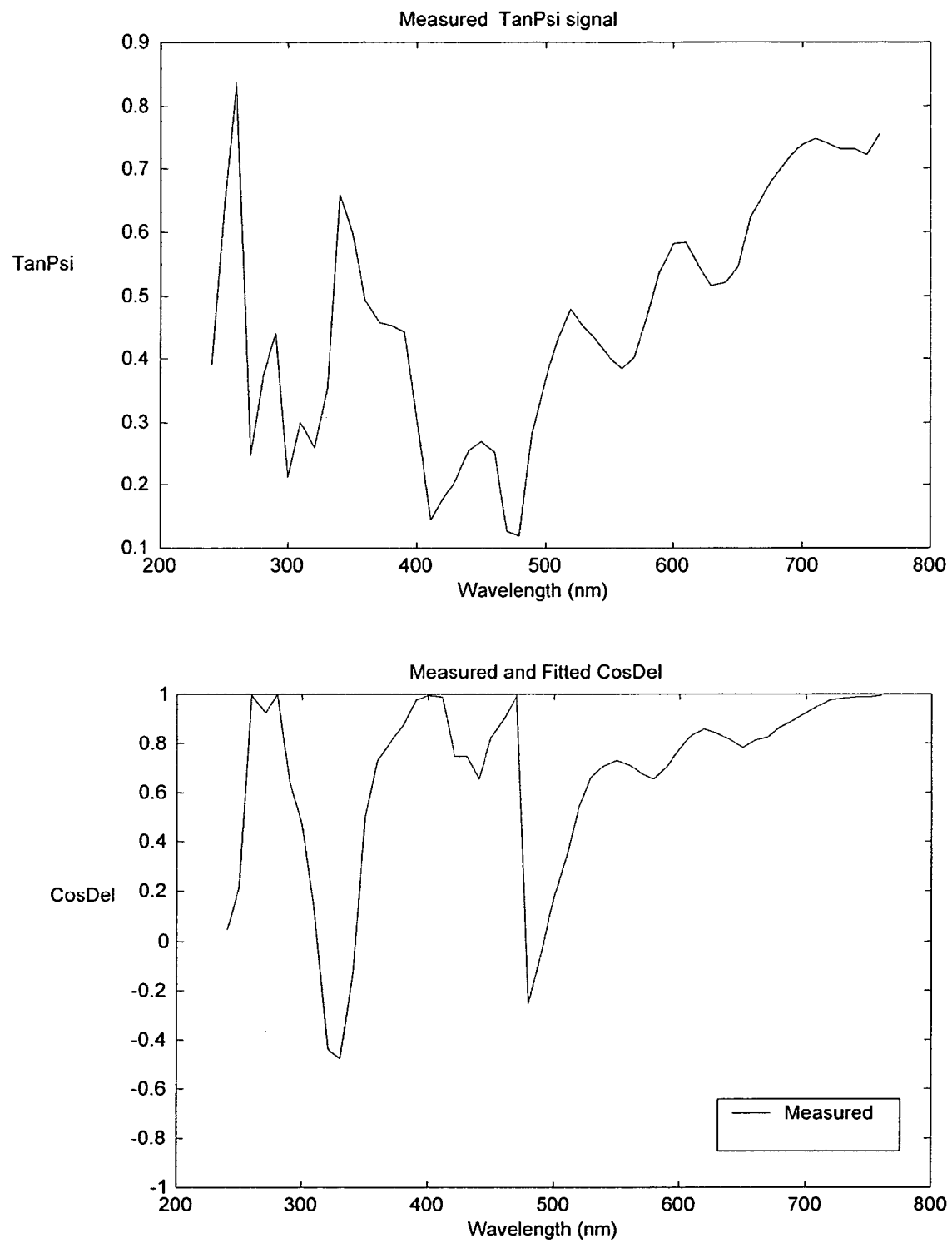
FIG. 18 illustrates phase and intensity signals recorded from a complex reflected and refracted light produced when an incident light is directed onto a surface, in accordance with an aspect of the present invention.

To illustrate the principles described above, reference is now made to FIGS. 13 through 18. Referring initially to FIG. 13, an incident light 902 is directed at a surface 900, upon which one or more features 906 may exist. The incident light 902 is reflected as reflected light 904. The properties of the surface 900, including but not limited to, thickness, uniformity, planarity, chemical composition and the presence of features, can affect the reflected light 904. The features 906 are raised upon the surface 900. The phase and intensity of the reflected light 904 can be measured and plotted, as shown, for example, in FIG. 18. The phase of the reflected light 904 can be plotted, as can the intensity of the reflected light 904. Such plots can be employed to compare measured signals with signatures stored in a signature library using techniques like pattern matching, for example.

Figure 14:
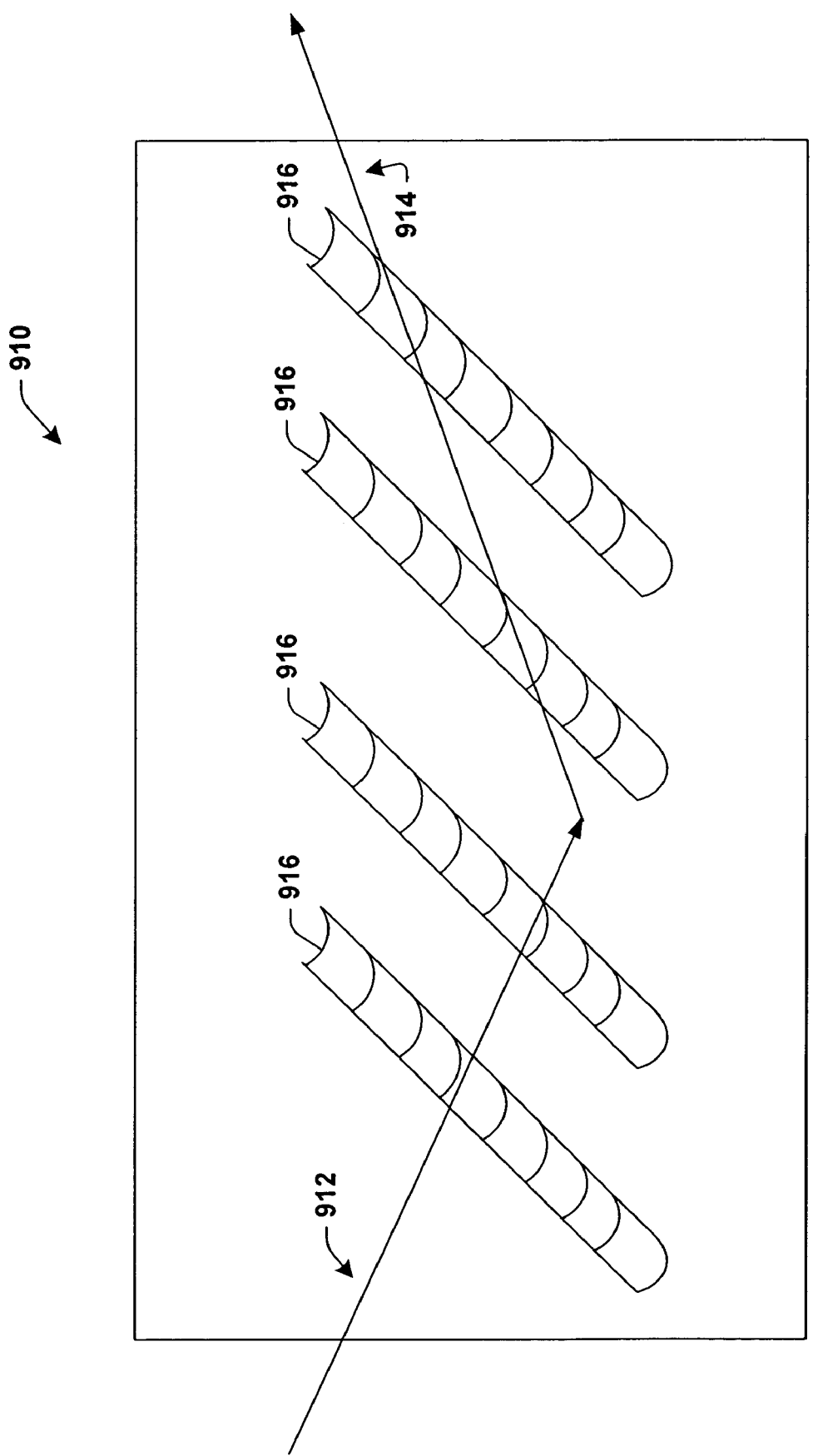
FIG. 14 is a simplified perspective view of an incident light reflecting off a surface, in accordance with an aspect of the present invention.

Referring now to FIG. 14, an incident light 912 is directed onto a surface 910 upon which one or more depressions 916 appear. The incident light 912 is reflected as reflected light 914. Like the one or more features 906 (FIG. 13) may affect an incident beam, so too may the one or more depressions 916 affect an incident beam. Thus, it is to be appreciated that scatterometry can be employed to measure features appearing on a surface, features appearing in a surface, and properties of a surface itself, regardless of features.

Figure 15:
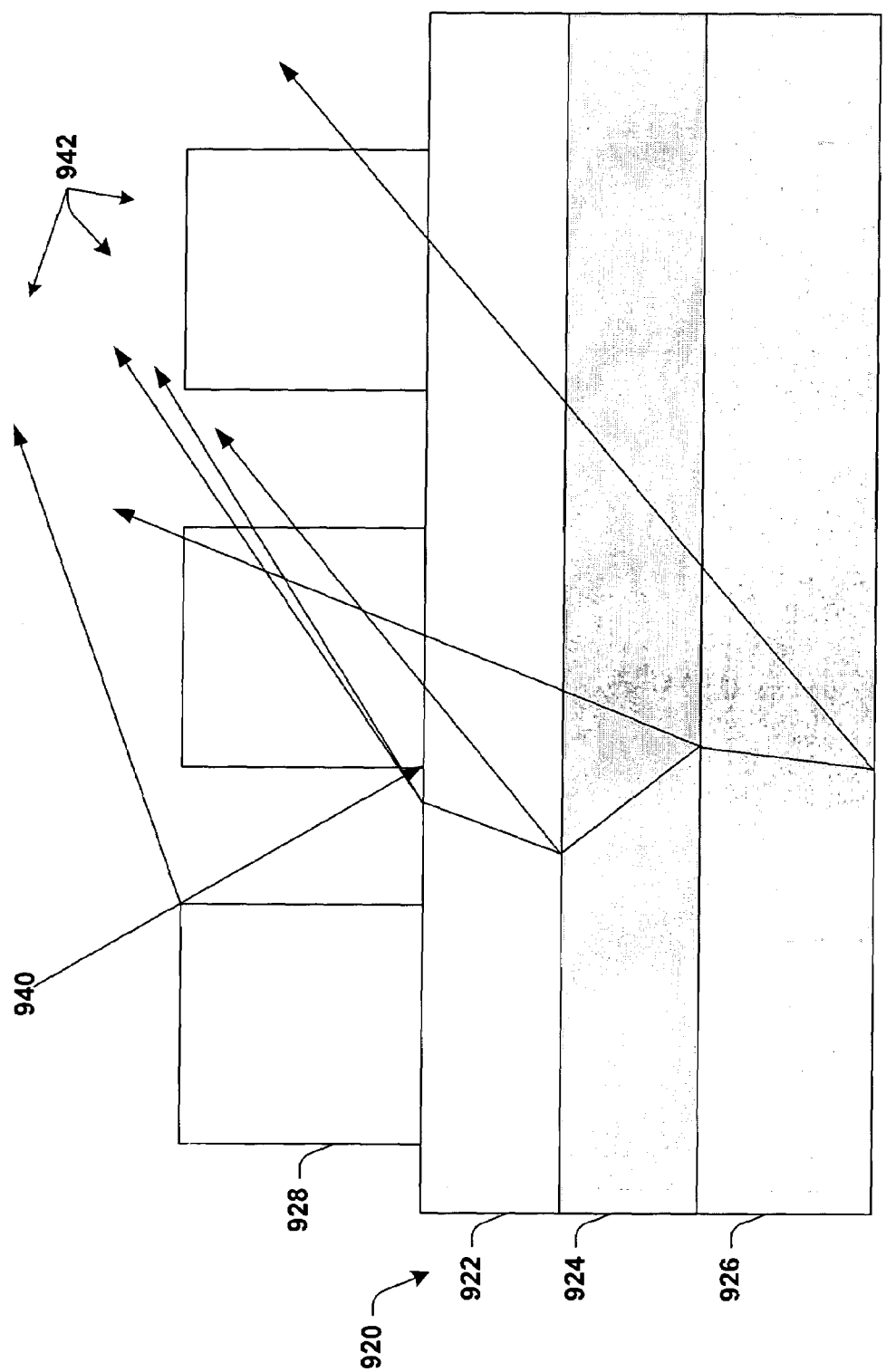
FIG. 15 illustrates a complex reflected and refracted light produced when an incident light is directed onto a surface, in accordance with an aspect of the present invention.

Turning now to FIG. 15, complex reflections and refractions of an incident light 940 are illustrated. The reflection and refraction of the incident light 940 can be affected by factors including, but not limited to, the presence of one or more features 928, and the composition of the substrate 920 upon which the features 928 reside. For example, properties of the substrate 920 including, but not limited to the thickness of a layer 922, the chemical composition of the layer 922, the opacity and/or reflectivity of the layer 922, the thickness of a layer 924, the chemical composition of the layer 924, the opacity and/or reflectivity of the layer 924, the thickness of a layer 926, the chemical composition of the layer 926, and the opacity and/or reflectivity of the layer 926 can affect the reflection and/or refraction of the incident light 940. Thus, a complex reflected and/or refracted light 942 may result from the incident light 940 interacting with the features 928, and/or the layers 922, 924 and 926. Although three layers 922, 924 and 926 are illustrated, it is to be appreciated that a substrate can be formed of a greater or lesser number of such layers.

Figure 16:
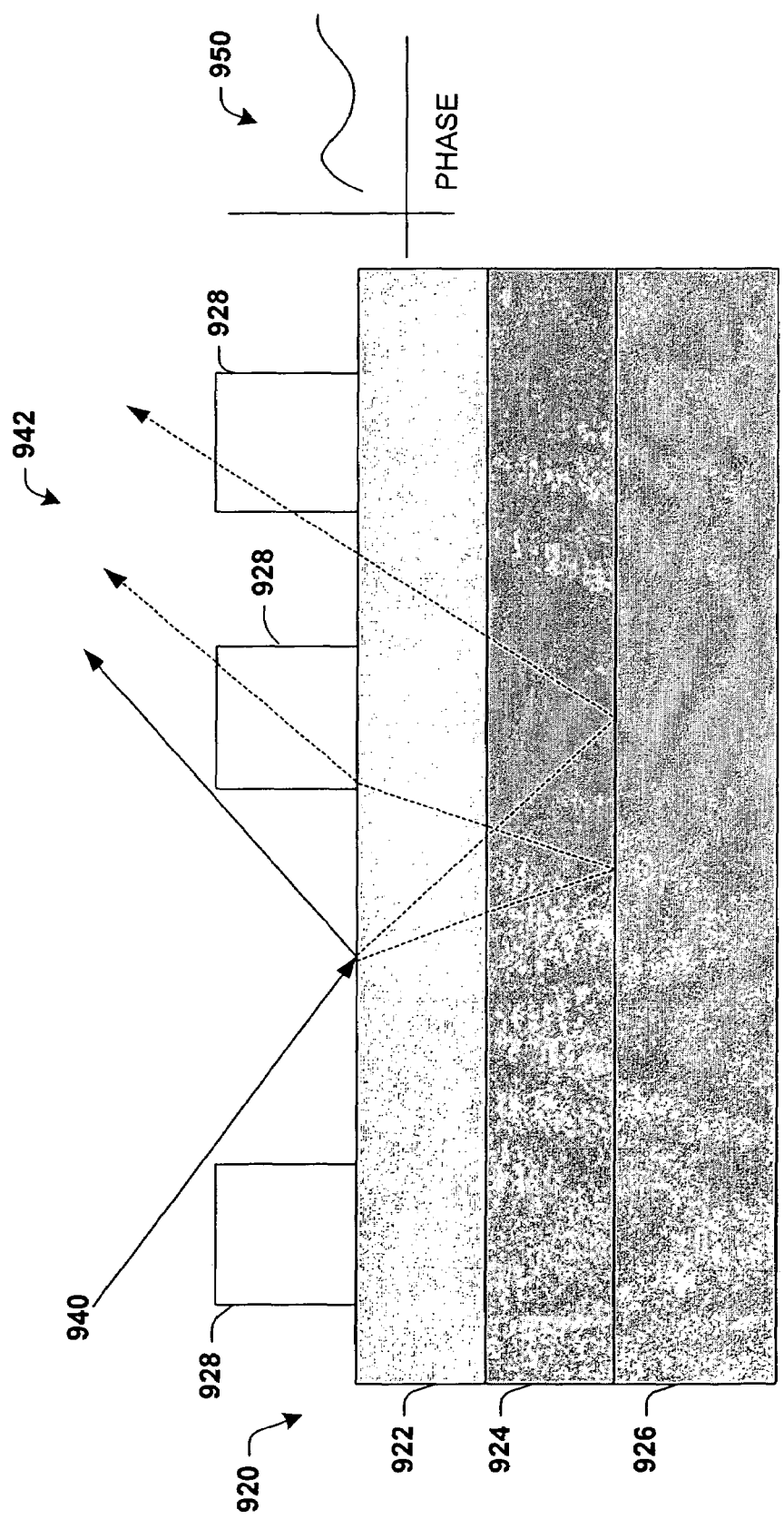
FIG. 16 illustrates a complex reflected and refracted light produced when an incident light is directed onto a surface, in accordance with an aspect of the present invention.
Figure 17:
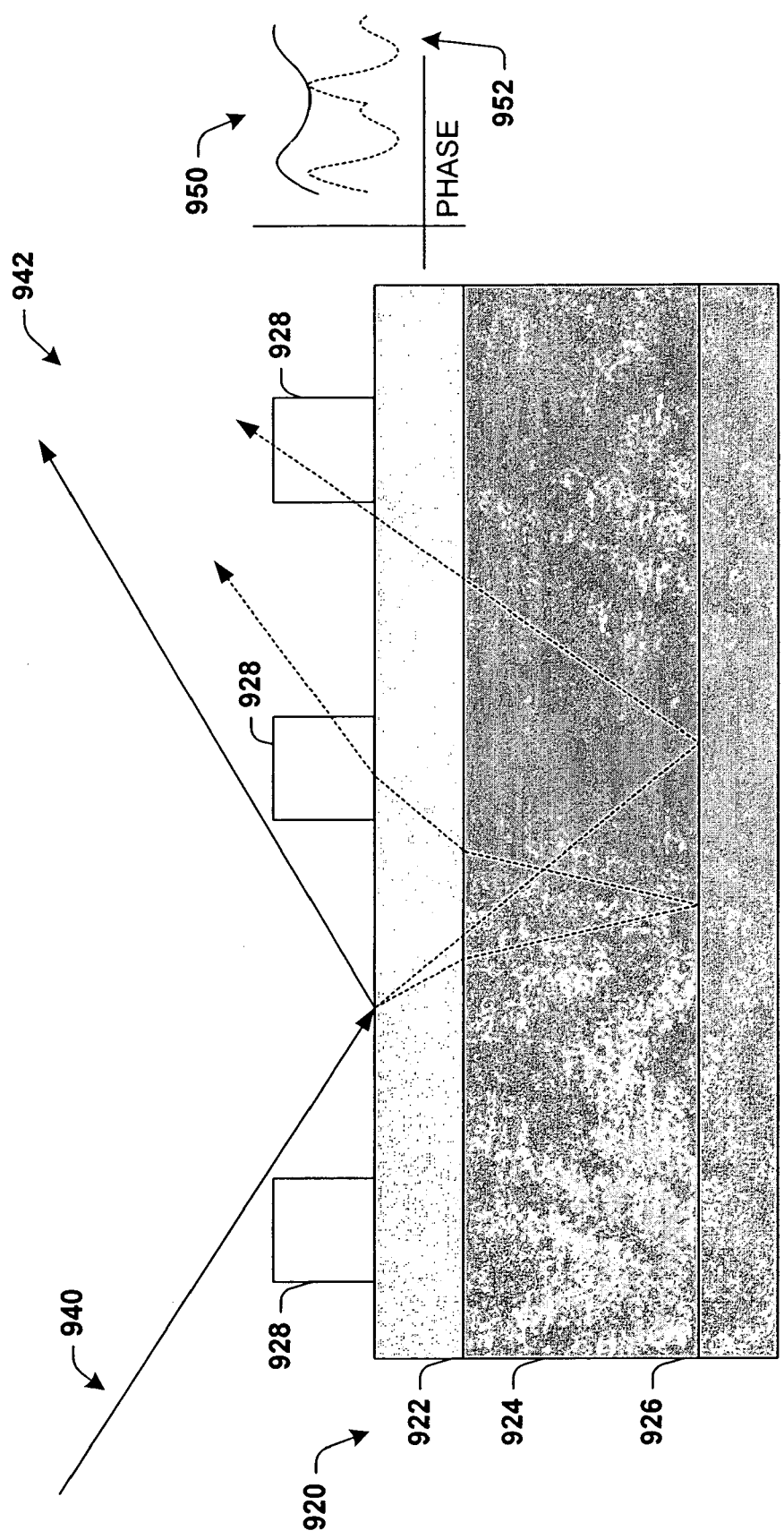
FIG. 17 illustrates a complex reflected and refracted light produced when an incident light is directed onto a surface, in accordance with an aspect of the present invention.

Turning now to FIG. 16, one of the properties from FIG. 15 is illustrated in greater detail. The substrate 920 can be formed of one or more layers 922, 924 and 926. The phase 950 of the reflected and/or refracted light 942 can depend, at least in part, on the thickness of a layer, for example, the layer 924. Thus, in FIG. 17, the phase 952 of a reflected light 942 differs from the phase 950 due, at least in part, to the different thickness of the layer 924 in FIG. 17 from the thickness of the layer 924 in FIG. 16.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for controlling a thin film deposition process, comprising:
    one or more thin film deposition components that deposit a thin film on one or more portions of a wafer;
    a thin film deposition component driving system for driving the one or more deposition components;
    a system for directing light on to the deposited thin film and collecting light reflected from the deposited thin film;
    a scatterometry system that detects structural irregularities associated with the deposited thin film by comparing reflected light data associated with the deposited thin film with a database comprising known thin film reflected light signatures; and
    a processor that communicates with the scatterometry system and the thin film deposition component driving system, the processor analyzes the deposited thin film by partitioning a conceptual mask into a plurality of grid blocks mapped on the wafer and determines deposition parameter adjustments for the one or more deposition components, the deposition parameter adjustments based at least in part upon data received from the scatterometry system.

2. The system of claim 1, the scatterometry system captures the light reflected from the thin film.

3. The system of claim 1, the structural irregularities associated with the thin film include at least one of pinholes, depressions, air bubbles, bumps, voids, agglomerates, large grains, second phase compositional variations and impurities, or a combination thereof.

4. The system of claim 1, the processor further determines the deposition parameter adjustments based in part on a presence of an unacceptable thin film deposition condition at the one or more grid blocks according to the data received from the scatterometry system.

5. The system of claim 1, the deposition parameter adjustments comprise at least one of thickness, uniformity, rate of deposition, pressure, flow rates of reacting species, flow rate of carrier gas and temperature or a combination thereof.

6. A method for monitoring and controlling the deposition of a thin film, comprising:
    depositing the thin film at a plurality of portions of a wafer;
    using a processor to partition the thin film into one or more conceptual grid blocks;
    directing a light within the one or more grid blocks associated with the thin film;
    collecting a light reflected from the one or more grid blocks associated with the thin film;
    employing a scatterometry system to analyze the reflected light from the one or more grid blocks associated with the thin film to determine one or more properties of the thin film;
    monitoring structural irregularities of the deposited thin film by comparing reflected light data collected from the one or more grid blocks associated with the thin film with a database comprising known thin film reflected light signatures;
    controlling a deposition component to deposit thin film at the one or more portions of on the wafer by utilizing a non-linear training system which facilitates determining deposition parameter adjustments according to the properties of the thin film; and
    using the processor to determine deposition conditions at the one or more portions of the wafer and to control the at least one deposition component based at least in part on data received from the scatterometry system.

7. The method of claim 6, the properties include at least one of thickness, uniformity, presence of defects, and presence of impurities or a combination thereof.

8. A method for regulating a process for depositing a thin film, comprising:
    using one or more deposition components to deposit a thin film;
    using a processor to partition the thin film into one or more conceptual monitoring zones;
    determining the characteristics of the deposited thin film at the one or more monitoring zones by utilizing reflected light to generate a signature and comparing the signature to known thin film reflected light signatures; and using the processor to coordinate control of the one or more deposition components to deposit subsequent thin film, the coordination based at least in part on the characteristics of the deposited thin film data gathered from comparing the reflected light from the one or more monitoring zones to known thin film light signatures.

9. A system for regulating a process for depositing a thin film, comprising:

means for using one or more deposition components to deposit a thin film;

means for determining the acceptability of the thin film deposition at one or more grid blocks by utilizing reflected light and comparing to known thin film reflected light signatures; and means for using a processor to map the thin film into one or more grid blocks on a conceptual coordinate system to coordinate control of the one or more deposition components to deposit the thin film, and to determine the acceptability of the thin film deposition by comparing the known thin film signatures to reflected light.

10. A system that controls the deposition of a thin film on a wafer, comprising:

at least one deposition component employed to deposit a thin film at one or more portions of the wafer;

a coherent light source directed onto one or more conceptual grid blocks of the thin film;

a receiving component that collects light reflected from the thin film;

a scatterometry system that analyzes the reflected light to determine one or more properties of the thin film at the one or more grid blocks; and a processor that controls the at least one deposition component based at least in part on data received from the scatterometry system.

* * * * *